United States Patent
Marek et al.

(10) Patent No.: US 9,585,584 B2
(45) Date of Patent: Mar. 7, 2017

(54) PHYSIOLOGICAL SIGNAL MONITOR WITH RETRACTABLE WIRES

(71) Applicant: Medicomp, Inc., Melbourne, FL (US)

(72) Inventors: Monte Marek, Palm Bay, FL (US); Sara England, Melbourne, FL (US); Anthony Balda, Satellite Beach, FL (US); George Koos, Melbourne Beach, FL (US)

(73) Assignee: Medicomp, Inc., Melbourne, FL (US)

( * ) Notice: Subject to any disclaimer, the term of this patent is extended or adjusted under 35 U.S.C. 154(b) by 0 days.

(21) Appl. No.: 14/987,323

(22) Filed: Jan. 4, 2016

(65) Prior Publication Data

US 2016/0113535 A1    Apr. 28, 2016

Related U.S. Application Data

(63) Continuation-in-part of application No. 14/616,801, filed on Feb. 9, 2015, now Pat. No. 9,226,679, which
(Continued)

(51) Int. Cl.
*A61B 5/0408* (2006.01)
*A61B 5/044* (2006.01)
(Continued)

(52) U.S. Cl.
CPC .......... *A61B 5/0408* (2013.01); *A61B 5/0006* (2013.01); *A61B 5/044* (2013.01);
(Continued)

(58) Field of Classification Search
CPC ... A61B 5/0404; A61B 5/0408; A61B 5/0006; A61B 2562/221; A61B 5/6826;
(Continued)

(56) References Cited

U.S. PATENT DOCUMENTS 4,606,352 A    8/1986    Geddes et al.
4,622,979 A    11/1986    Katchis et al.
(Continued)

FOREIGN PATENT DOCUMENTS

CN    101278833 A    10/2008
EP    2664273 A1    11/2013
(Continued)

OTHER PUBLICATIONS

WIPO, "International Application Publication without International Search Report for PCT Application Serial No. PCT/U516/27310 filed Apr. 13, 2016", Oct. 20, 2016. (36 Pages).
(Continued)

*Primary Examiner* — Mark W Bockelman
(74) *Attorney, Agent, or Firm* — Mark Malek; Kelly Swartz; Widerman Malek, PL

(57) ABSTRACT

A physiological signal monitor having retractable wires may include a housing, a patch and a cradle. The housing may be adapted to carry a memory, a first electrical contact, a second electrical contact, and a processor in data communication with the memory. The patch may include a first side adapted to be secured to a patient and an opposing second side. The cradle connects to the second side of the patch and may be adapted to carry the housing. The cradle may include a wire retractor, a first electrical pad adapted to contact the first electrical contact, a second electrical pad adapted to contact the second electrical contact, a first sensing connector, a second sensing connector, a first wire connecting the first electrical pad to the first sensing connector, and a second wire connecting the second electrical pad to the second sensing connector.

20 Claims, 11 Drawing Sheets

Related U.S. Application Data is a continuation of application No. 13/111,517, filed on May 19, 2011, now Pat. No. 8,989,850.

(60) Provisional application No. 61/347,117, filed on May 21, 2010, provisional application No. 62/146,740, filed on Apr. 13, 2015.

(51) Int. Cl.
  *A61B 5/00* (2006.01)
  *A61B 5/0432* (2006.01)
  *A61B 5/0404* (2006.01)

(52) U.S. Cl.
  CPC .......... *A61B 5/0404* (2013.01); *A61B 5/0432* (2013.01); *A61B 5/04325* (2013.01); *A61B 5/6823* (2013.01); *A61B 5/6826* (2013.01); *A61B 2560/045* (2013.01); *A61B 2562/221* (2013.01)

(58) Field of Classification Search
  CPC . A61B 2560/045; A61B 5/044; A61B 5/0432; A61B 5/04325
  See application file for complete search history.

(56) References Cited

U.S. PATENT DOCUMENTS

| | | | |
|---|---|---|---|
| 4,858,617 A | 8/1989 | Sanders | |
| 4,938,228 A | 7/1990 | Righter et al. | |
| 4,947,846 A | 8/1990 | Kitagawa et al. | |
| 5,307,818 A | 5/1994 | Segalowitz | |
| 5,398,183 A | 3/1995 | Elliott | |
| 5,730,143 A | 3/1998 | Schwarzberg | |
| 5,813,979 A | 9/1998 | Wolfer et al. | |
| 5,931,791 A | 8/1999 | Saltzstein et al. | |
| 5,941,829 A | 8/1999 | Saltzstein et al. | |
| 5,959,529 A | 9/1999 | Kail | |
| 6,117,077 A | 9/2000 | Del Mar et al. | |
| 6,225,901 B1 | 5/2001 | Kail | |
| 6,287,252 B1 | 9/2001 | Lugo | |
| 6,456,872 B1 | 9/2002 | Faisandier | |
| 6,496,715 B1 | 12/2002 | Lee et al. | |
| 6,546,285 B1 | 4/2003 | Owen et al. | |
| 6,567,680 B2 | 5/2003 | Swetlik et al. | |
| 6,569,095 B2 | 5/2003 | Eggers | |
| 6,605,046 B1 * | 8/2003 | Del Mar ............ A61B 5/04085 128/917 | |
| 6,664,893 B1 | 12/2003 | Eveland et al. | |
| 6,665,385 B2 | 12/2003 | Rogers et al. | |
| 6,690,959 B2 | 2/2004 | Thompson | |
| 6,694,177 B2 | 2/2004 | Eggers et al. | |
| 6,801,137 B2 | 10/2004 | Eggers | |
| 6,871,089 B2 | 3/2005 | Korzinov et al. | |
| 6,897,788 B2 | 5/2005 | Khair et al. | |
| 6,940,403 B2 | 9/2005 | Kail | |
| 6,957,107 B2 | 10/2005 | Rogers et al. | |
| 6,987,965 B2 | 1/2006 | Ng et al. | |
| 7,002,468 B2 | 2/2006 | Eveland et al. | |
| 7,092,750 B2 | 8/2006 | Van Ess | |
| 7,099,715 B2 | 8/2006 | Korzinov et al. | |
| 7,130,396 B2 | 10/2006 | Rogers et al. | |
| 7,194,300 B2 | 3/2007 | Korzinov | |
| 7,206,630 B1 | 4/2007 | Tarler | |
| 7,212,850 B2 | 5/2007 | Prystowsky et al. | |
| 7,257,438 B2 | 8/2007 | Kinast | |
| 7,286,865 B2 | 10/2007 | Nazeri | |
| 7,299,085 B2 | 11/2007 | Bergelson et al. | |
| 7,382,247 B2 | 6/2008 | Welch et al. | |
| 7,444,177 B2 | 10/2008 | Nazeri | |
| 7,554,828 B2 | 6/2009 | Wilson | |
| 7,587,237 B2 | 9/2009 | Korzinov et al. | |
| 7,668,588 B2 | 2/2010 | Kovacs | |
| 7,729,753 B2 | 6/2010 | Kremliovsky et al. | |
| 7,764,988 B2 | 7/2010 | Drew et al. | |
| D621,048 S | 8/2010 | Severe et al. | |
| 7,787,943 B2 | 8/2010 | McDonough | |
| D634,431 S | 3/2011 | Severe et al. | |
| 7,907,996 B2 | 3/2011 | Prystowsky et al. | |
| 7,941,207 B2 | 5/2011 | Korzinov | |
| 7,970,450 B2 | 6/2011 | Kroecker et al. | |
| 7,996,075 B2 | 8/2011 | Korzinov et al. | |
| 8,016,776 B2 | 9/2011 | Bourget et al. | |
| 8,068,914 B1 * | 11/2011 | Walsh .................. A61N 1/0541 607/136 | |
| 8,108,033 B2 | 1/2012 | Drew et al. | |
| 8,116,841 B2 | 2/2012 | Bly et al. | |
| 8,160,682 B2 | 4/2012 | Kumar et al. | |
| 8,160,703 B2 | 4/2012 | Stickney et al. | |
| D659,836 S | 5/2012 | Bensch et al. | |
| 8,200,319 B2 | 6/2012 | Pu et al. | |
| 8,214,007 B2 | 7/2012 | Baker et al. | |
| 8,239,012 B2 | 8/2012 | Felix et al. | |
| 8,249,686 B2 | 8/2012 | Libbus et al. | |
| 8,255,046 B2 | 8/2012 | Sarkar et al. | |
| 8,273,053 B2 | 9/2012 | Saltzstein | |
| RE43,767 E | 10/2012 | Eggers et al. | |
| 8,285,356 B2 | 10/2012 | Bly et al. | |
| 8,285,370 B2 | 10/2012 | Felix et al. | |
| 8,290,129 B2 | 10/2012 | Rogers et al. | |
| 8,315,687 B2 | 11/2012 | Cross et al. | |
| 8,374,688 B2 | 2/2013 | Libbus et al. | |
| 8,425,414 B2 | 4/2013 | Eveland | |
| 8,444,578 B2 | 5/2013 | Bourget et al. | |
| 8,449,469 B2 | 5/2013 | Banet et al. | |
| 8,449,471 B2 | 5/2013 | Tran | |
| 8,460,189 B2 | 6/2013 | Libbus et al. | |
| 8,473,039 B2 | 6/2013 | Michelson et al. | |
| 8,483,809 B2 | 7/2013 | Kim et al. | |
| 8,506,480 B2 | 8/2013 | Banet et al. | |
| 8,515,529 B2 | 8/2013 | Pu et al. | |
| 8,538,503 B2 | 9/2013 | Kumar et al. | |
| 8,550,997 B2 | 10/2013 | Talbot et al. | |
| 8,560,040 B2 | 10/2013 | Gehman et al. | |
| 8,560,046 B2 | 10/2013 | Kumar et al. | |
| 8,565,864 B2 | 10/2013 | Drew et al. | |
| 8,611,980 B2 | 12/2013 | Choe et al. | |
| 8,613,708 B2 | 12/2013 | Bishay et al. | |
| 8,613,709 B2 | 12/2013 | Bishay et al. | |
| 8,620,402 B2 | 12/2013 | Parker et al. | |
| 8,626,262 B2 | 1/2014 | McGusty et al. | |
| 8,630,699 B2 | 1/2014 | Baker et al. | |
| 8,639,319 B2 | 1/2014 | Hugh et al. | |
| 8,663,106 B2 | 3/2014 | Stivoric et al. | |
| 8,688,189 B2 | 4/2014 | Shennib | |
| 8,688,190 B2 | 4/2014 | Libbus et al. | |
| 8,718,752 B2 | 5/2014 | Libbus et al. | |
| 8,734,339 B2 | 5/2014 | Rao et al. | |
| 8,744,562 B2 | 6/2014 | Giftakis et al. | |
| 8,773,258 B2 | 7/2014 | Vosch et al. | |
| 8,782,308 B2 | 7/2014 | Vlach | |
| 8,790,257 B2 | 7/2014 | Libbus et al. | |
| 8,795,174 B2 | 8/2014 | Manicka et al. | |
| 8,798,728 B2 | 8/2014 | Drew et al. | |
| 8,814,792 B2 | 8/2014 | Raptis et al. | |
| 8,818,481 B2 | 8/2014 | Bly et al. | |
| 8,823,490 B2 | 9/2014 | Libbus et al. | |
| 8,838,218 B2 | 9/2014 | Khair | |
| 8,897,868 B2 | 11/2014 | Mazar et al. | |
| 8,909,832 B2 | 12/2014 | Vlach et al. | |
| 8,945,019 B2 | 2/2015 | Prystowsky et al. | |
| 8,965,492 B2 | 2/2015 | Baker et al. | |
| 8,965,498 B2 | 2/2015 | Katra et al. | |
| 8,989,850 B2 | 3/2015 | Balda | |
| 9,017,255 B2 | 4/2015 | Raptis et al. | |
| 9,021,161 B2 | 4/2015 | Vlach et al. | |
| 9,044,148 B2 | 6/2015 | Michelson et al. | |
| 9,241,635 B2 | 1/2016 | Yuen et al. | |
| 2002/0045836 A1 | 4/2002 | Alkawwas | |
| 2002/0067256 A1 | 6/2002 | Kail | |
| 2004/0006265 A1 | 1/2004 | Alhussiny | |
| 2004/0077954 A1 | 4/2004 | Oakley et al. | |
| 2004/0260189 A1 | 12/2004 | Eggers et al. | |
| 2005/0049515 A1 | 3/2005 | Misczynski et al. | |

(56) References Cited

U.S. PATENT DOCUMENTS

| | | |
|---|---|---|
| 2005/0113661 A1 | 5/2005 | Nazeri et al. |
| 2005/0119580 A1 | 6/2005 | Eveland |
| 2006/0030781 A1 | 2/2006 | Shennib |
| 2006/0030782 A1 | 2/2006 | Shennib |
| 2006/0069320 A1 | 3/2006 | Wolff et al. |
| 2006/0095091 A1 | 5/2006 | Drew |
| 2006/0276715 A1 | 12/2006 | Yeo et al. |
| 2007/0129769 A1 | 6/2007 | Bourget et al. |
| 2007/0149887 A1 | 6/2007 | Hwang et al. |
| 2007/0156054 A1 | 7/2007 | Korzinov et al. |
| 2007/0293776 A1 | 12/2007 | Korzinov et al. |
| 2008/0097231 A1 | 4/2008 | Balda et al. |
| 2008/0108890 A1 | 5/2008 | Teng et al. |
| 2008/0177168 A1 | 7/2008 | Callahan et al. |
| 2008/0275327 A1 | 11/2008 | Faarbaek et al. |
| 2009/0062670 A1 | 3/2009 | Sterling et al. |
| 2009/0076342 A1 | 3/2009 | Amurthur et al. |
| 2010/0056881 A1 | 3/2010 | Libbus et al. |
| 2010/0168578 A1 | 7/2010 | Garson et al. |
| 2010/0249541 A1 | 9/2010 | Geva et al. |
| 2010/0249624 A1 | 9/2010 | Peng |
| 2010/0249625 A1 | 9/2010 | Lin |
| 2010/0268103 A1 | 10/2010 | McNamara et al. |
| 2010/0317958 A1 | 12/2010 | Beck et al. |
| 2011/0144470 A1 | 6/2011 | Mazar et al. |
| 2011/0160601 A1 | 6/2011 | Wang et al. |
| 2011/0166464 A1 | 7/2011 | Lee et al. |
| 2011/0218418 A1 | 9/2011 | Green et al. |
| 2011/0270100 A1 | 11/2011 | Chang |
| 2012/0022387 A1* | 1/2012 | Balda ............. A61B 5/0006 600/523 |
| 2012/0029313 A1 | 2/2012 | Burdett et al. |
| 2012/0089001 A1 | 4/2012 | Bishay et al. |
| 2012/0101396 A1 | 4/2012 | Solosko et al. |
| 2012/0197150 A1 | 8/2012 | Cao et al. |
| 2012/0330126 A1 | 12/2012 | Hoppe et al. |
| 2013/0030259 A1 | 1/2013 | Thomsen et al. |
| 2013/0060098 A1 | 3/2013 | Thomsen et al. |
| 2013/0109937 A1 | 5/2013 | Banet et al. |
| 2013/0116520 A1 | 5/2013 | Roham et al. |
| 2013/0116533 A1 | 5/2013 | Lian et al. |
| 2013/0116585 A1 | 5/2013 | Bouguerra |
| 2013/0150698 A1 | 6/2013 | Hsu et al. |
| 2013/0204100 A1 | 8/2013 | Acquista |
| 2013/0225967 A1 | 8/2013 | Esposito |
| 2013/0226018 A1 | 8/2013 | Kumar et al. |
| 2013/0231577 A1 | 9/2013 | Leiderman |
| 2013/0245415 A1 | 9/2013 | Kumar et al. |
| 2013/0274584 A1 | 10/2013 | Finlay et al. |
| 2013/0289424 A1 | 10/2013 | Brockway et al. |
| 2013/0296667 A1 | 11/2013 | Rastegar et al. |
| 2013/0331678 A1 | 12/2013 | Lading et al. |
| 2013/0338448 A1 | 12/2013 | Libbus et al. |
| 2014/0094676 A1 | 4/2014 | Gani et al. |
| 2014/0100432 A1 | 4/2014 | Golda et al. |
| 2014/0128712 A1 | 5/2014 | Banet et al. |
| 2014/0128713 A1 | 5/2014 | Banet et al. |
| 2014/0128714 A1 | 5/2014 | Banet et al. |
| 2014/0128757 A1 | 5/2014 | Banet et al. |
| 2014/0206976 A1 | 7/2014 | Thompson et al. |
| 2014/0206977 A1 | 7/2014 | Bahney et al. |
| 2014/0213879 A1 | 7/2014 | Choe et al. |
| 2014/0221772 A1 | 8/2014 | Wolloch et al. |
| 2014/0236249 A1 | 8/2014 | Rao et al. |
| 2014/0249443 A1 | 9/2014 | Banet et al. |
| 2014/0275928 A1 | 9/2014 | Acquista et al. |
| 2014/0275932 A1 | 9/2014 | Zadig |
| 2014/0288385 A1 | 9/2014 | Amurthur et al. |
| 2014/0330088 A1 | 11/2014 | Libbus et al. |
| 2014/0350362 A1 | 11/2014 | Raptis et al. |
| 2014/0371604 A1 | 12/2014 | Katra et al. |
| 2014/0378799 A1 | 12/2014 | Chattaraj et al. |
| 2015/0005588 A1 | 1/2015 | Herken et al. |
| 2015/0005589 A1 | 1/2015 | Bly et al. |
| 2015/0005590 A1 | 1/2015 | Libbus et al. |
| 2015/0018657 A1 | 1/2015 | Bibian et al. |
| 2015/0022372 A1 | 1/2015 | Vosch |
| 2015/0057512 A1 | 2/2015 | Kapoor |
| 2015/0073252 A1 | 3/2015 | Mazar |
| 2015/0087921 A1 | 3/2015 | Felix et al. |
| 2015/0087922 A1 | 3/2015 | Bardy et al. |
| 2015/0087923 A1 | 3/2015 | Bardy et al. |
| 2015/0087949 A1 | 3/2015 | Felix et al. |
| 2015/0087950 A1 | 3/2015 | Felix et al. |
| 2015/0087951 A1 | 3/2015 | Felix et al. |
| 2015/0094552 A1 | 4/2015 | Golda et al. |
| 2015/0094556 A1 | 4/2015 | Geva et al. |
| 2015/0094557 A1 | 4/2015 | Hsu et al. |
| 2015/0094558 A1 | 4/2015 | Russell |
| 2015/0094559 A1 | 4/2015 | Russell |
| 2015/0094605 A1 | 4/2015 | Sabesan et al. |
| 2015/0105631 A1 | 4/2015 | Tran et al. |
| 2015/0105647 A1 | 4/2015 | Katra et al. |
| 2015/0126822 A1 | 5/2015 | Chavan et al. |
| 2015/0126848 A1 | 5/2015 | Baker et al. |
| 2015/0148622 A1 | 5/2015 | Moyer et al. |
| 2015/0148637 A1 | 5/2015 | Golda et al. |
| 2015/0148691 A1 | 5/2015 | Moyer et al. |
| 2015/0150505 A1 | 6/2015 | Kaskoun et al. |
| 2015/0150506 A1 | 6/2015 | Woo |
| 2015/0297134 A1 | 10/2015 | Albert et al. |

FOREIGN PATENT DOCUMENTS

| | | |
|---|---|---|
| GB | 2458389 A | 9/2009 |
| KR | 20140050374 A | 4/2014 |
| KR | 20140088390 A | 7/2014 |
| WO | WO 99/59465 | 11/1999 |
| WO | WO2007094729 A1 | 8/2007 |
| WO | WO2008005016 A1 | 1/2008 |
| WO | WO2011146708 A2 | 11/2011 |
| WO | WO2014116816 A1 | 7/2014 |

OTHER PUBLICATIONS

USPTO, "International Search Report for PCT Application Serial No. PCT/US16/27310 filed Apr. 13, 2016", Nov. 14, 2016, 2 pages.

USPTO, "Written Opinion for PCT Application Serial No. PCT/US16/27310 filed Apr. 13, 2016", Nov. 14, 2016, 4 pages.

\* cited by examiner

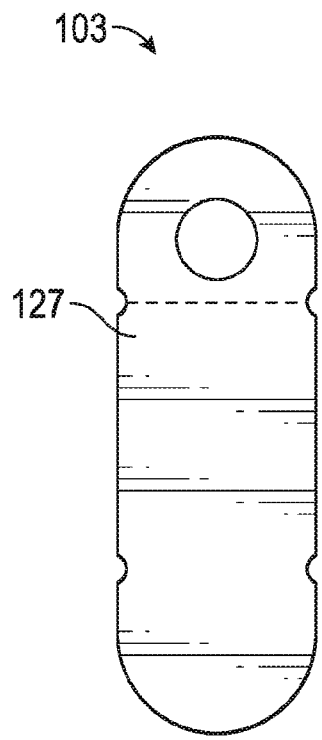
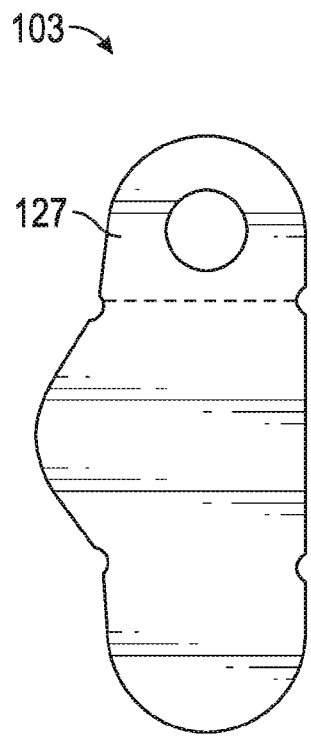
FIG. 9          FIG. 10
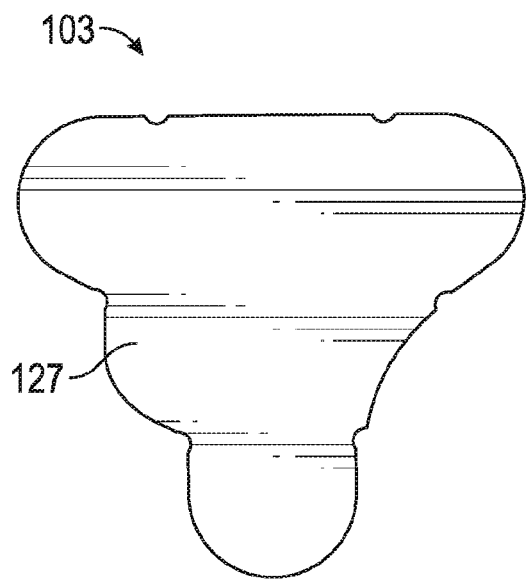
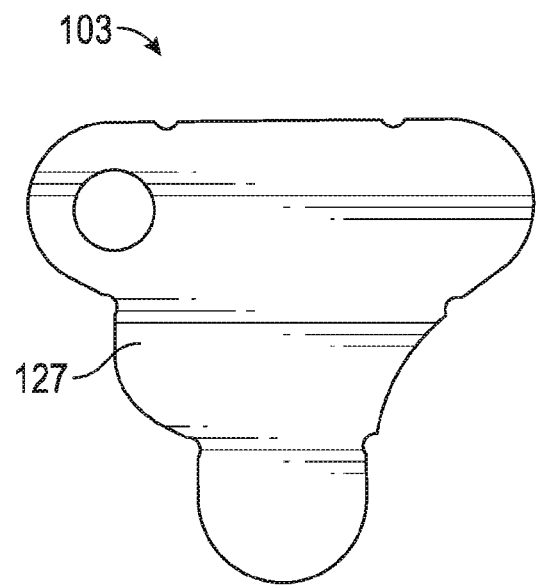
FIG. 11         FIG. 12

PHYSIOLOGICAL SIGNAL MONITOR WITH RETRACTABLE WIRES

RELATED APPLICATIONS

This application is a continuation in part and claims the benefit under 35 U.S.C. §120 of U.S. patent application Ser. No. 14/616,801 filed on Feb. 9, 2015 and titled Systems and Methods for Interelectrode Distance Optimization in a Retractable Multi-Use Cardiac Monitor, which in turn claimed the benefit under 35 U.S.C. §119(e) of U.S. patent application Ser. No. 13/111,517 (now U.S. Pat. No. 8,989, 850) filed on May 19, 2011 and titled Retractable Multi-Use Cardiac Monitor, which in turn claimed the benefit under 35 U.S.C. §119(e) of U.S. Provisional Patent Application No. 61/347,117, filed on May 21, 2010 and titled Retractable Multi-Use Cardiac Monitor. This application also claims the benefit under 35 U.S.C. §119(e) of U.S. Provisional Patent Application No. 62/146,740, filed on Apr. 13, 2015 and titled Pendant Physiological Signal Monitor and Associated System and Methods. The entire contents of each of which are incorporated herein by reference to the extent that they do not conflict with the disclosure herein.

FIELD OF THE INVENTION

The present invention relates generally to the field of cardiac monitoring. Specifically, the present invention is directed towards a retractable multi-use cardiac monitor.

BACKGROUND

Cardiac monitoring systems are generally comprised of a series of electrodes attached to the chest area of a patient to collect electrocardiogram (ECG) data. The series of electrodes are usually connected to a series of wires. However, the series of electrodes and interconnected wires may not be provided in a compact portable form that allows for easy adjustment of a vector length between the electrodes.

Accordingly, there is a need for a retractable multi-use cardiac monitor that is compact in form and allows for easy adjustment of the vector length between the electrodes of the retractable multi-use cardiac monitor.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention provide a physiological signal monitor having retractable wires. The physiological signal monitor may include a housing, a patch, and a cradle. The housing may be adapted to carry, a memory, a first electrical contact, a second electrical contact, and a processor in data communication with the memory. The patch may include a first side adapted to be secured to a patient and an opposing second side. The cradle may be connected to the second side of the patch and adapted to carry the housing. The cradle may include a wire retractor, a first electrical pad adapted to contact the first electrical contact, a second electrical pad adapted to contact the second electrical contact, a first sensing connector, a second sensing connector, a first wire connecting the first electrical pad to the first sensing connector, wherein the wire retractor is configured to extend and retract the first wire to vary a linear distance between the first electrical pad and the first sensing connector, and a second wire connecting the second electrical pad to the second sensing connector, wherein the wire retractor is configured to extend and retract the second wire to vary a linear distance between the second electrical pad and the second sensing connector. The first sensing connector and the second sensing connector may be configured to collect ECG data and store ECG data onto the memory.

The housing may include a symptom button.

The first and second sensing connectors may be configured to connect to wearable electrodes.

The first and second sensing connectors may be shaped to receive a finger.

The physiological signal monitor may include a third sensing connector located on the first side of the patch and configured to collect ECG data and store ECG data onto the memory. The housing may include a third electrical contact. The cradle may include a third electrical pad adapted to contact the third electrical contact and in electrical communication with the third sensing connector.

The physiological signal monitor may include a wireless radio configured to transmit a portion of collected ECG data from the memory to a destination. The destination may be a smart phone or a monitoring center.

The physiological signal monitor may include a display screen that is configured to display collected ECG data.

The housing may detachably connect to the cradle.

The housing may be adapted to accommodate ten channels of ECG data,

The wire retractor may be flexibly connected to the housing.

BRIEF DESCRIPTION OF THE DRAWINGS

FIG. 2b is a rear perspective view of the housing as depicted in FIG. 2a.

FIG. 9 is a front elevation view of a patch of the physiological signal monitor according to an embodiment of the present invention.

FIG. 10 is a front elevation view of a patch of the physiological signal monitor according to an embodiment of the present invention.

FIG. 11 is a front elevation view of a patch of the physiological signal monitor according to an embodiment of the present invention.

FIG. 12 is a front elevation view of a patch of the physiological signal monitor according to an embodiment of the present invention.

DETAILED DESCRIPTION OF THE INVENTION

Figure 1:
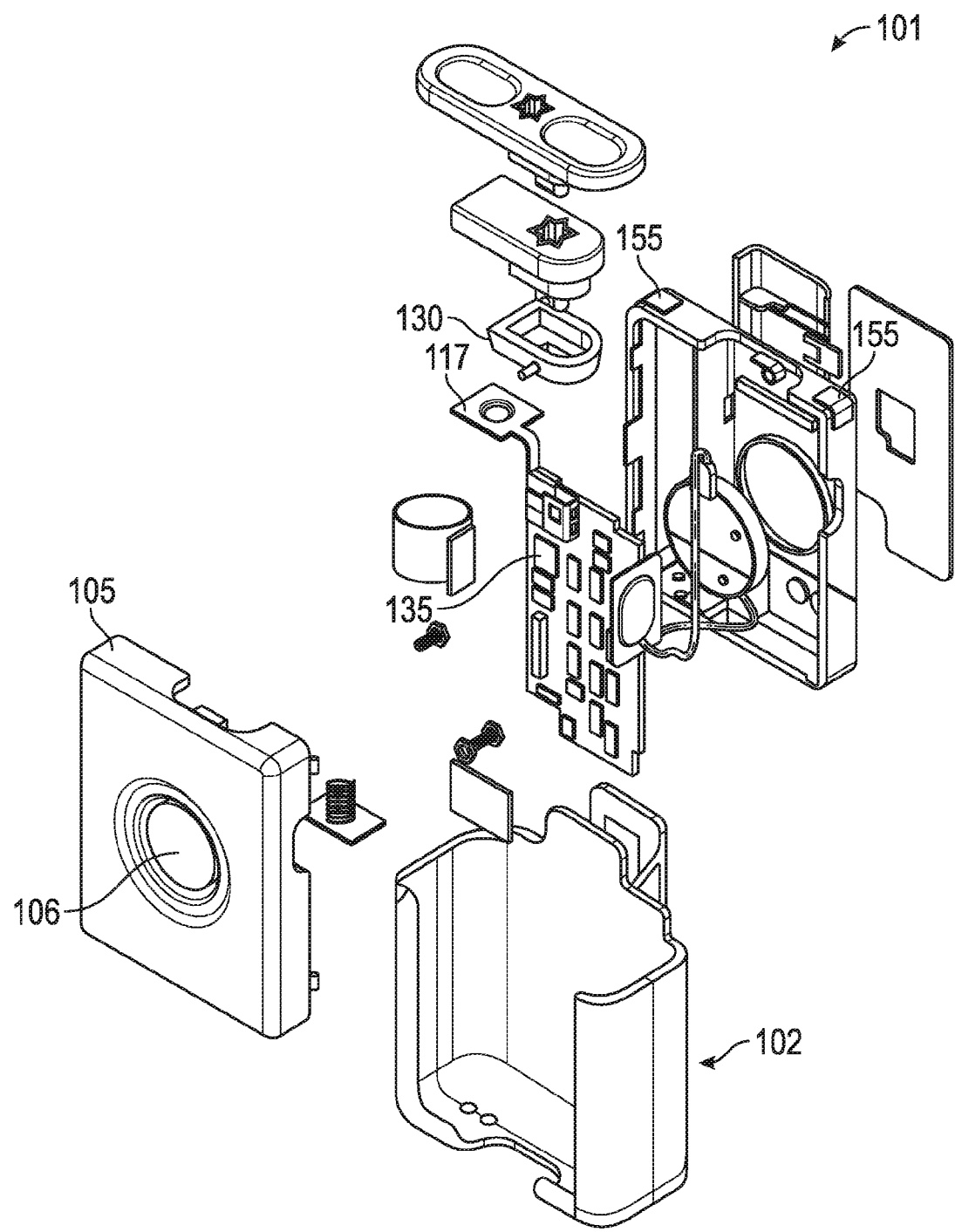
FIG. 1 is an exploded view of a housing of a physiological signal monitor according to an embodiment of the present invention.
Figure 2A:
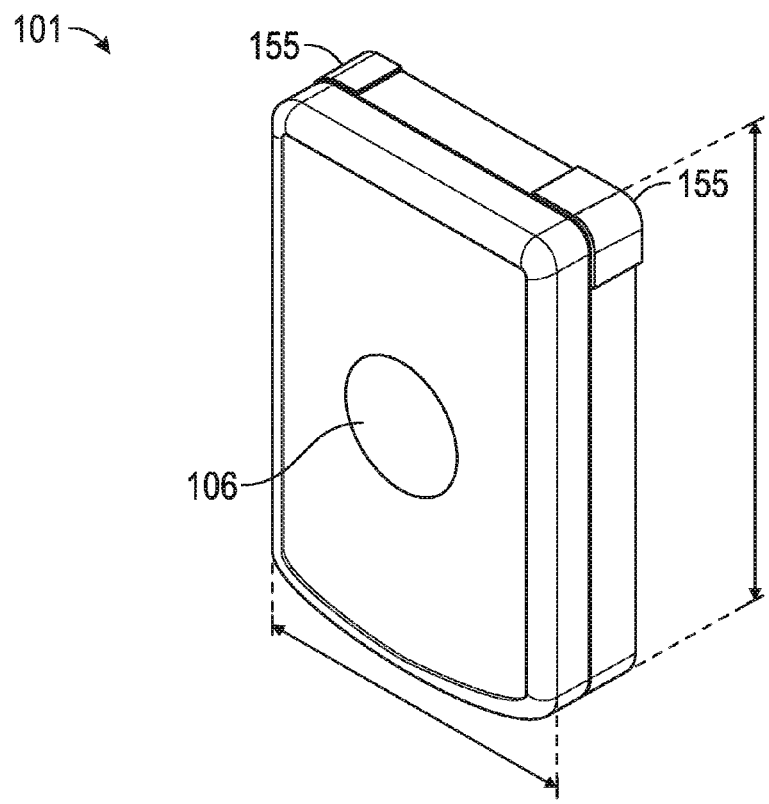
FIG. 2a is a front perspective view of a housing of the physiological signal monitor according to an embodiment of the present invention.
Figure 2B:
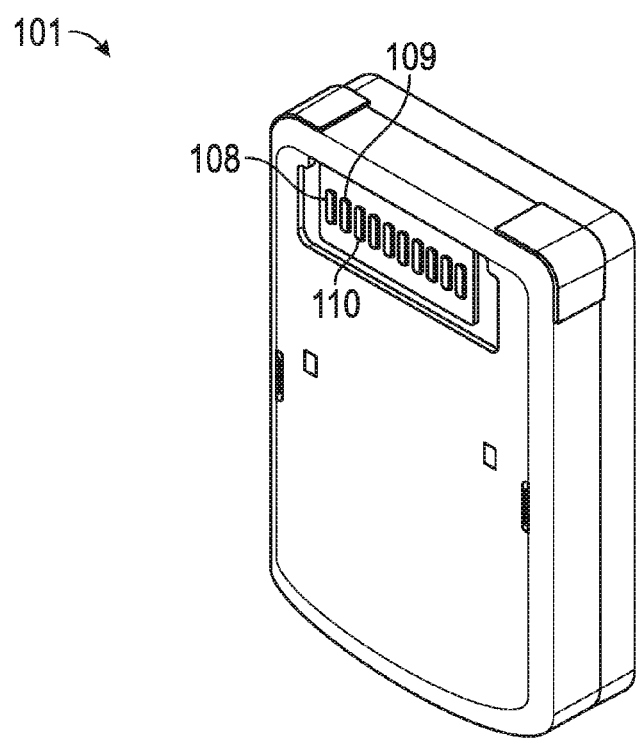
Figure 3:
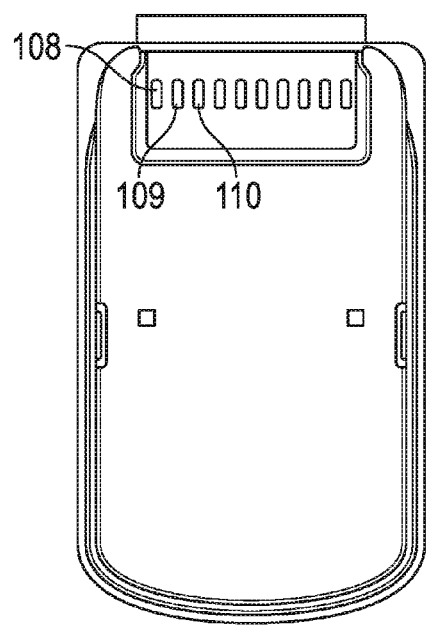
FIG. 3 is a front perspective view of a housing of the physiological signal monitor according to an embodiment of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides a device, system, or method capable of advantageously harvesting and monitoring physiological signals. This device may be used in a formal medical setting (medically prescribed form), or as an over-the-counter (OTC) device available for commercial sale to the public for those interested in general health and fitness.

An embodiment of a physiological signal monitor 100 system may comprise three main components: a first component, hereinafter referred to as a housing 101, comprising electrical elements that may be carried by the housing 101; a second component, hereinafter referred to as a cradle 102, comprising a device to which the housing 101 may be configured to removably attach, and a third component, hereinafter referred to as a patch 103, comprising a device adapted to secure to a patient and carry the cradle 102. A person of ordinary skill in the art would recognize that the housing 101 disclosed herein may be deployed in combination with any number of physically and electrically compatible carrier designs (as described below).

Referring now to FIGS. 1-4, according to one embodiment of the present invention, a housing 101 may advantageously feature a water resistant compartment 105. By way of example, and not as a limitation, the housing 101 may comprise a device interface 130 that may facilitate interchangeable connectivity with the carrier component, such as, by way of example, and without limitation, a cable harness 140, a 3-wire cradle, a 5-wire cradle, a retractable monitor device, or a finger electrode adapter. Any of these carrier components may be integrated with the cradle 102 or the patch 103.

Other features of the housing 101, according to various embodiments of the present invention, may include one or more of the following electrical elements: patient symptom button 106, memory 107, electrical contacts 108, 109, 110, and a processor 111.

The electrical elements of the housing 101 may be configured to deliver overall device functionality. For example, and without limitation, the housing 101 may be configured to carry circuitry necessary to advantageously perform biosignal harvest, evaluation, and intercommunication activities. For example, and without limitation, the electrical elements of the housing 101 may have the ability to harvest, record, and/or analyze some number or types of input data channels at a given instance in time. In one embodiment, the housing 101 may be adapted to accommodate up to ten channels of ECG data. Also by way of example, and not as a limitation, the electrical elements of the housing 101 may be configured to perform data extraction, system updates, and other data manipulation capacities via wireless data transmission (e.g., cellular network communication, BlueTooth, Zigbee, WiFi) and/or via wired connection (e.g., USB, microUSB) to computing equipment external to the device. The housing 101 may also comprise a user interface (by way of example, and not as a limitation, one or more of integrated fingertip ECG electrodes 155, display screen, touch-screen display, indicator lights, power switch/button, and recording activation button).

Figure 4:
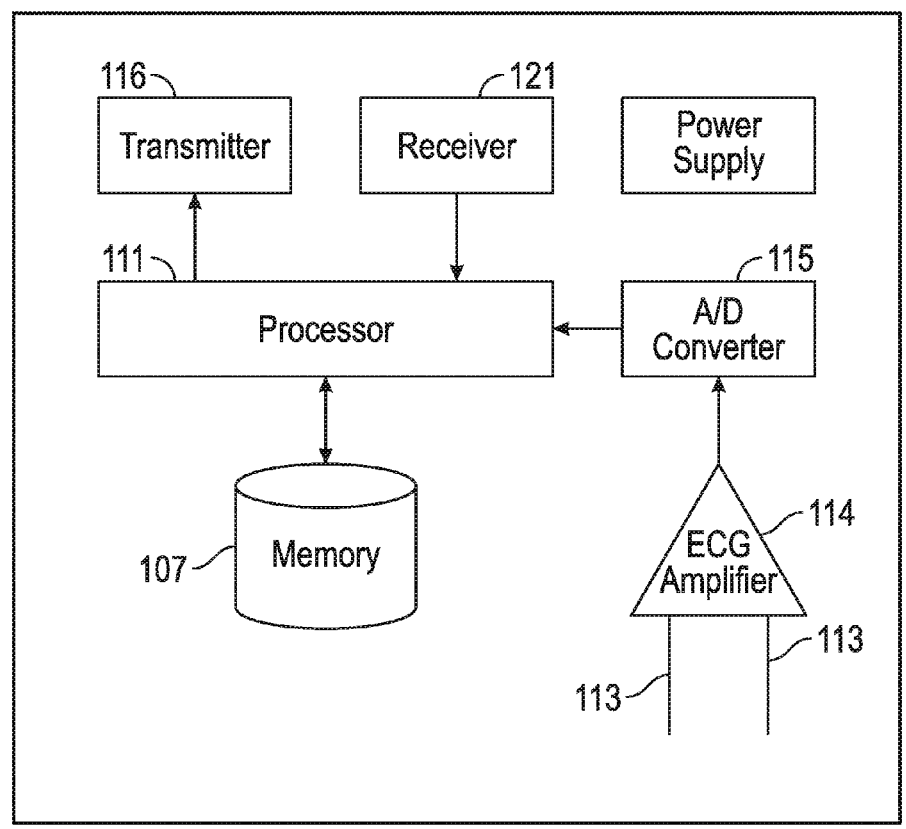
FIG. 4 is a block diagram of a system on a chip (SoC) as implemented in a physiological signal monitor according to an embodiment of the present invention.
Figure 5:
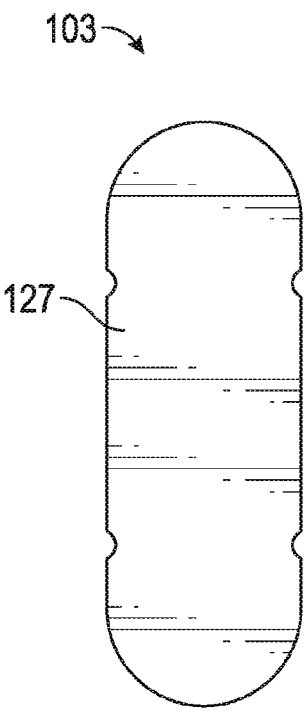
FIG. 5 is a front elevation view of a patch of the physiological signal monitor according to an embodiment of the present invention.
Figure 6:
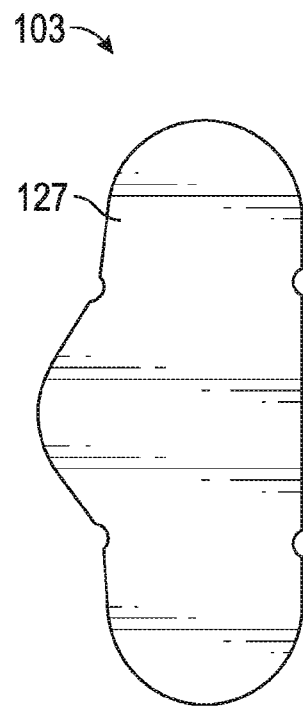
FIG. 6 is a front elevation view of a patch of the physiological signal monitor according to an embodiment of the present invention.
Figure 7:
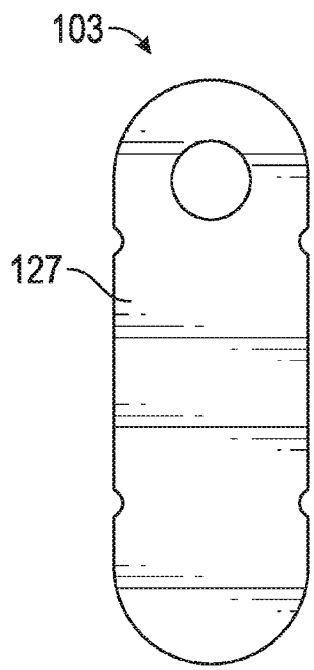
FIG. 7 is a front elevation view of a patch of the physiological signal monitor according to an embodiment of the present invention.
Figure 8:
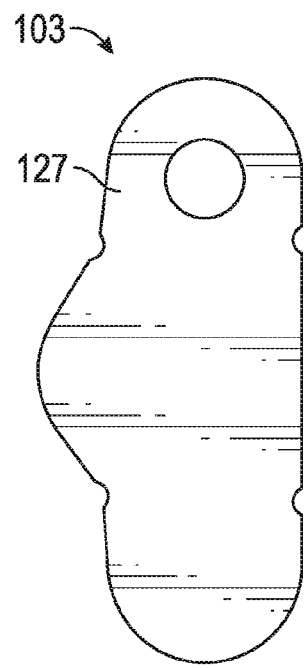
FIG. 8 is a front elevation view of a patch of the physiological signal monitor according to an embodiment of the present invention.
Figure 13:
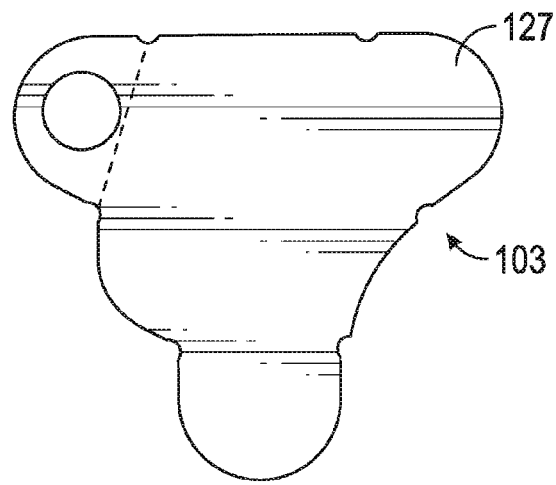
FIG. 13 is a front elevation view of a patch of the physiological signal monitor according to an embodiment of the present invention.

Referring now to FIG. 4, the housing 101 may include at least one input connector 113 that may be adapted to connect one or more electrical contacts, 108 109, 110, to a signal amplifier 114. The amplifier 114 may come into electrical contact with a conductor of an ECG lead. For example, and without limitation, the amplifier 114 may receive signals from the conductor via an integrated wiring system. The signals from the conductor may be amplified and subsequently converted by an A/D converter 115. For example, and without limitation, the A/D converter 115 may be configured to digitize the signals from the amplifier 114, and may optionally include filters to filter the signals or perform signal processing and identification of physiological conditions. The amplified and converted signals may be directed into processing and storage circuitry that may include a memory 107 or a processor 111 to implement filtering and processing functions to provide intermediate results and to store information before transmission to computing resources outside of the housing 101. For example, and without limitation, filtering and processing functions employed on computing resources either local to the housing 101 or remote from the housing 101 may be configured to execute algorithms as described by the related applications incorporated by reference herein. In one such embodiment, the pre-processing circuitry of the housing 101 may electrically couple the processed signals to a transmitter 116 (which may include the integrated antenna 117), which may transmit the signals to a base station 120, wireless router 118 or directly to a cellular network 119. The signals may be transmitted using, for example, Zigbee or Bluetooth protocols, to a base station 120 that may be a computer, personal data assistant (PDA), cellular phone, tablet, wireless phone, or the like. Other circuitry (not shown) may include timing and interface circuitry.

As related above, the electrical contacts 108, 109, and 110 may be in data communication with the memory 107, which may retain recorded signals until transmitted (transient) or may retain recorded signals until either manually or automatically deleted (persistent). The transmitter 116 may be configured to receive data from at least one of the electrical contacts 108, 109, and 110 and the memory 107, and to communicate the data representing electrical signals detected by the electrodes. Also for example, and without limitation, the housing 101 may carry a receiver 121 in electrical communication with the memory 107. The receiver 121 may be configured to receive data and route the data to the memory 107 through the processor 111. For example, and without limitation, both communication of data from the transmitter 116 and receipt of data by the receiver 121 may occur wirelessly using the integrated antenna 117 or over a wired connection. In one embodiment of wireless communication, the transmitter 116 or the receiver 121 may be implemented using radio frequency identification (RFID) technology.

In one embodiment, a first and second wire 122, 123 may be connected to a wire retractor 124 carried by the cradle 102 in such a manner that the first electrical contact 108, which may be secured to the first wire 122, and the second electrical contact 109, which may be secured to the second wire 123, may be exposed and readily accessible by the user. The first wire 122 and second wire 123 may be extendable and retractable from the wire retractor 124. In embodiments utilizing more than two electrodes, an additional wire may be included for each additional electrode. The electrodes may be secured to the electrical contacts secured to the wires. These electrodes may be placed on the body of the user in such a way that the contacts may be in position to harvest the desired physiological signal. Placement of the electrodes may be accomplished by the user or by another individual.

The cradle 102 component of the physiological signal monitoring system may comprise one of a potential multitude of cradles 102. Such cradles 102 may vary both in structure and in function, dependent on the physiological parameters to be measured. For example, and without limitation, each cradle 102 may have a common connection point, or similar mechanical and/or electrical attachment structure, that may advantageously allow for simple and easy connection of any physically and/or electrically compatible accessory to the housing 101 component. For example, and without limitation, both the housing 101 and the cradle 102 may comprise a standard external zero-insertion contact surface. The respective contact surfaces of the housing 101 and the cradle 102 may support electrical communication between these two components. The housing 101 may be detachably connected to the cradle 102.

The cradle 102 may have a wire retractor 124 adapted to extend or retract at least one wire 122, 123. The cradle 102 may have a different wire retractor 124 for each wire 122, 123 secured to the cradle 102. At least one wire retractor 124 may be flexibly connected to the housing 101. The cradle 102 may have electrical pads 132, 133, 134, adapted to contact electrical contacts 108, 109, 110 carried by the housing 101. Contact between an electrical pad 132, 133, 134 and an electrical contact 108, 109, 110 may provide electronic communication between the respective contact points.

Referring now to FIGS. 5-16, the cradle 102 may be carried by a flexible patch 103. For example, and without limitation, the flexile patch 103 may comprise some combination of a flexible printed circuit board (PCB) and a fabric overlay configured to advantageously facilitate user comfort when placed in contact with the user's skin. For example, and without limitation, the patch 103 may comprise a patch style ECG recorder. The ECG recorder may be external to the patch 103 and contained in a housing 101 carried by the cradle 102. In some embodiments, no electrode may be carried by the patch 103. In some embodiments, one or more electrodes may be carried by the patch 103. Data harvested from the patch 103 carried electrode, if present, may be received by the cradle 102 and electrically provided to the housing 101. In some embodiments, data from a patch 103 carried electrode may be received by the housing 101 in addition to electrode data received from a first electrical contact 108 or a second electrical contact 109 secured to the first wire 122 or second wire 123, respectively. The ECG recorder, or housing 101, may support both single and double channel procedures. The patch 103 may advantageously be wearable for seven (7) days without causing skin irritation and conform to the patients' contours. The patch 103 may feature water resistance during patient showering to advantageously support the seven day wear time. For example, and without limitation, the patch 103 may support a housing 101 and cradle 102 weight of 36 grams.

By way of example, and not as a limitation, the patch 103 may be designed without incorporated electrodes (see FIGS. 5, 6, 11 and 14), incorporating a single electrode (see FIGS. 7, 8-10, 12 and 13), as a single channel patch (see FIGS. 15 and 16), as a two channel patch, or as a patch 103 accommodating up to 10 channels. The patch 103 may have a first side secured to a patient 126 and a second, opposing, side 127 adapted to carry or connect to the cradle 102.

Regardless of whether the patch 103 carries one or more electrodes 128, ECG data may be collected by at least one electrode 128 connected to at least one sensing connector 129, 130, or 131 or by the sensing connector 129, 130, 131. The electrode 128 connected to the sensing connector may be a wearable electrode. The sensing connector may be shaped to receive a finger and collect ECG data from a patient's finger.

Figure 14:
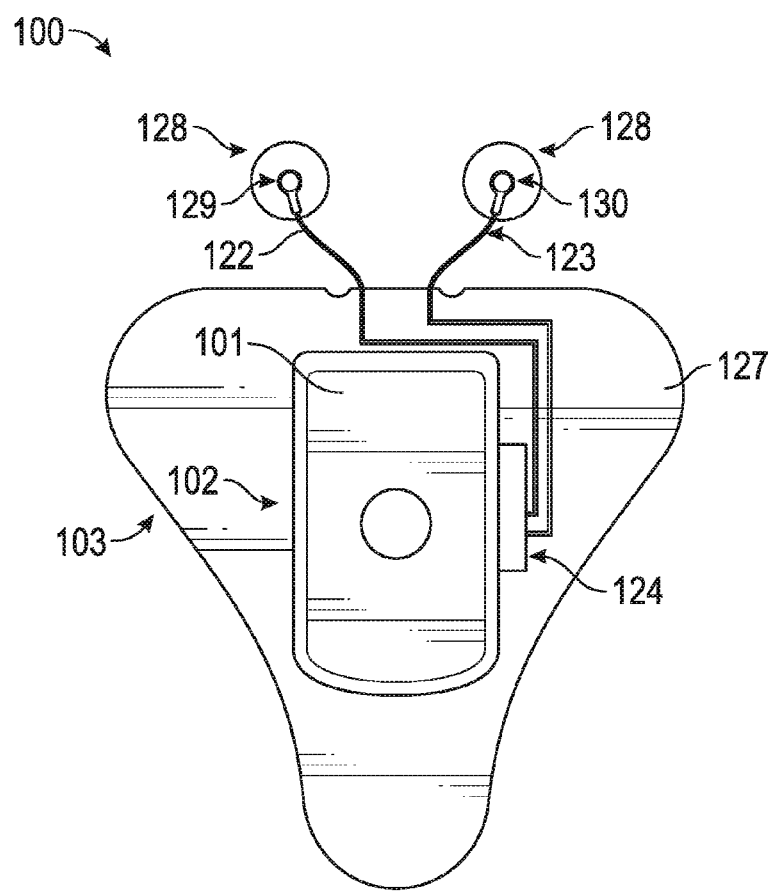
FIG. 14 is a front elevation view of the patch as depicted in FIG. 11 in combination with the housing as depicted in FIG. 2 and a cradle according to an embodiment of the present invention.
Figure 15:
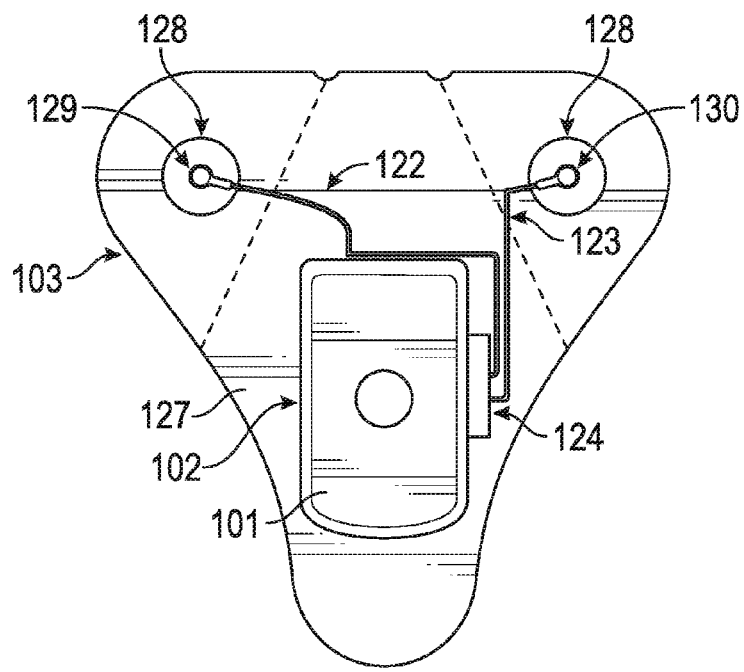
FIG. 15 is a front elevation view of the patch as depicted in FIG. 13 in combination with the housing as depicted in FIG. 2 and a cradle according to an embodiment of the present invention.
Figure 16:
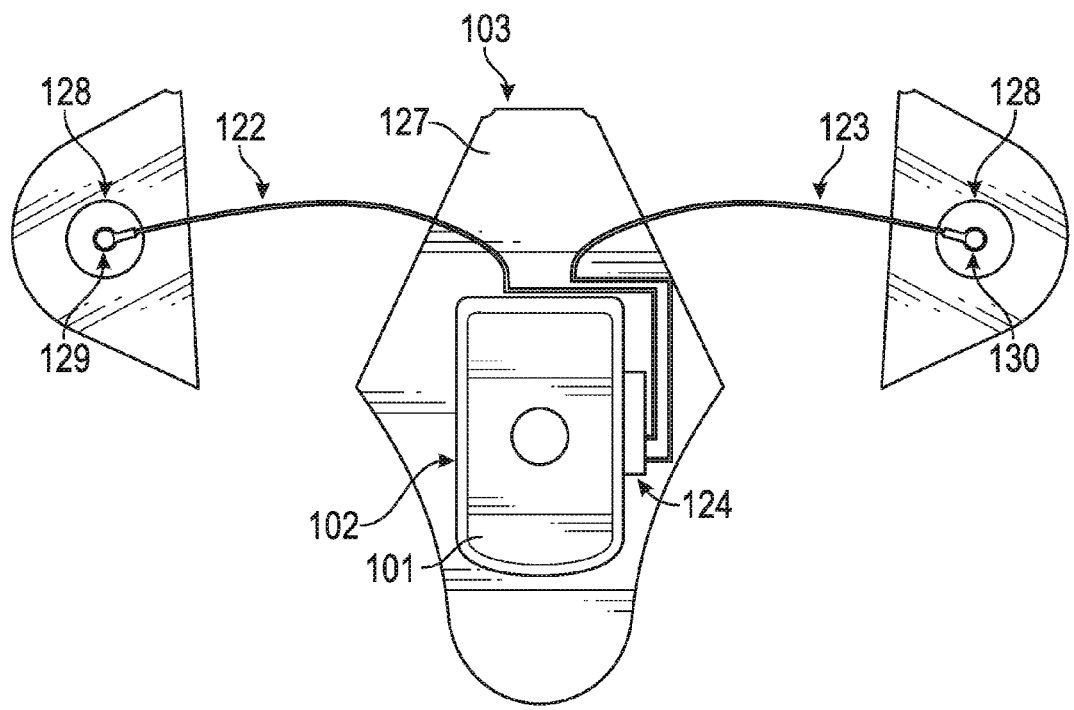
FIG. 16 is a front elevation view of the patch as depicted in FIG. 13, with detachable electrodes detached, in combination with the housing as depicted in FIG. 2 and a cradle according to an embodiment of the present invention.
Figure 17:
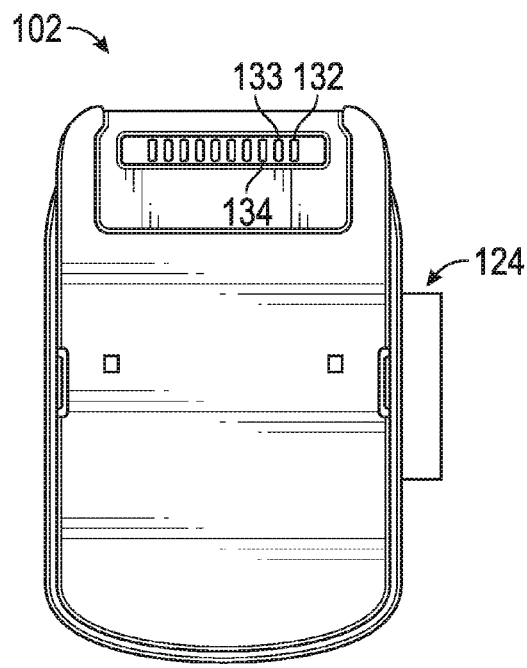
FIG. 17 is a front elevation view of the cradle as depicted in FIG. 16.
Figure 18:
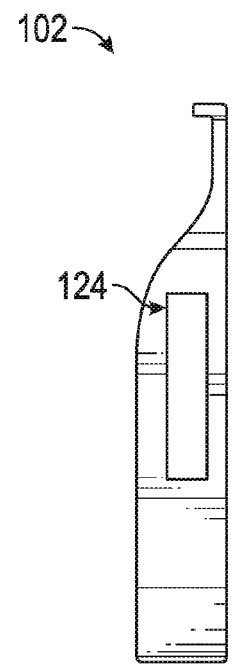
FIG. 18 is a side elevation view of the cradle as depicted in FIG. 16.
Figure 19:
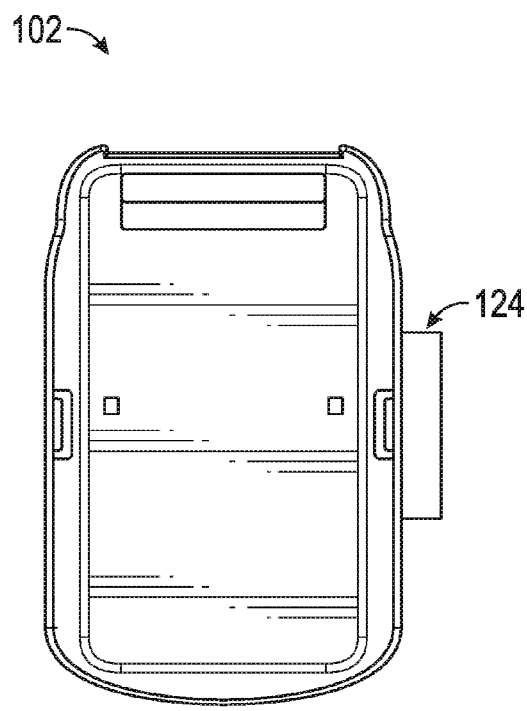
FIG. 19 is a rear elevation view of the cradle as depicted in FIG. 16.
Figure 20:
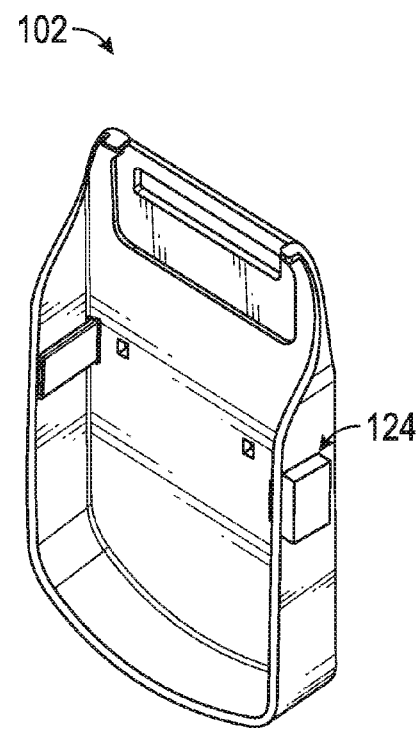
FIG. 20 is a front perspective view of the cradle as depicted in FIG. 16.

The cradle 102 may have a first wire 122 connecting a first sensing connector 129 to a first electrical pad 132. The first sensing connector 129 may be adapted to connect to an electrode 128 or other physiological sensor. The cradle 102 may have any number of wires and corresponding connectors and pads. As shown in FIG. 14, the cradle 102 has a first wire 122 and a second wire 123 connecting a first sensing connector 129 to a first electrical pad 132 and a second sensing connector 130 to a second electrical pad 133, respectively. A wire retractor 124 may be configured to extend or retract the first wire 122 and the second wire 123 to vary the linear distance between the electrical pad and the sensing connector connected by the wire. The wire may be extended to secure an electrode 128 to a patient 126 at a desired location. The wire may be retracted to eliminate loose wire impeding the movement or comfort of the patient 126.

The patch 103 may carry a third sensing connector 131 on the first side of the patch. The third sensing connector 131 may be adapted to connect to an electrode 128 or other physiological sensor. The third sensing connector 131 may be an electrode. The third sensing connector may be configured to collect ECG data and provide this data to the housing 101 for storage onto the memory 107. The third sensing connector 131 may be in electrical communication with a third electrical pad 134 located on the cradle 102. The third electrical pad 134 may be adapted to contact to third electrical contact 110 located on the housing 101 when the housing 102 is carried by the cradle 102.

In one embodiment, as shown in FIGS. 9, 10, and 13-15 the patch may carry at least one electrode 128 in one or more detachable portions of the patch 103. The detachable portion may be separated from the non-detachable portion or other detachable portions with perforations in the patch 103. The detachable portion may be removed or separated from the non-detachable portion or other detachable portions by tearing the patch 103 along the perforation. The electrode 128 carried by a detachable portion of the patch 103 may be secured to a sensing connector 129, 130 and electrically connected to an electrical pad 123, 133, 134 through a wire 122, 123. The wire may be connected to a wire retractor 124.

The cradle 102 may provide electrical connection to some number of electrodes coated in an electrically-conductive material (e.g., gold, Silver-Silver Chloride) and may be configured to electrically interconnect to the housing 101 via hard gold pads. Also for example, and without limitation, the patch 103 may include one or more ECG electrodes and may be secured to the patient's chest using adhesives applicable for the situation. Electrical connectivity of the ECG electrodes to the patch 103 or their respective sensing connectors 129, 130, 131 may be through pogo or small cantilever beam contacts that may be soldered to an interface board and configured in electrical contact with gold pads on the housing 101 when installed.

For example, and without limitation, the physiological signal monitor 100 may be made available in either a medically-prescribed form or as an over-the counter (OTC) device. In the prescribed form, the physiological signal monitor 100 may use one or more of its communication means mentioned previously to send the acquired data to a monitoring center. By way of example, and not as a limitation, a wireless radio 135 may be carried by the housing 101 and configured to transmit at least a portion of collected ECG data from the memory 107 to a destination. Again, by way of example, and not as a limitation, the destination may be a smart phone 136, a base station 120, a cellular network 119, a monitoring center, or the like. For example, and without limitation, the monitoring center may feature human over read, or no human over read (e.g., fully automated monitoring). For example, and without limitation, the monitoring center may analyze and process the data through a proprietary software system and process, and reports may be generated and sent to a physician, or the data may be sent directly to the physician in raw form and/or as an automatically configured report. The information may also be transmitted to a mobile device application which may be downloaded by a user onto her own instance of the physiological signal monitoring system. For example, and without limitation, the mobile device application may be able to send data over data networks (see App-Based Carrier and Data-Routing disclosure below) to the appropriate monitoring center, physician, or other downstream user, and may eliminate the need for the patient to carry a second mobile device in addition to her own.

In another embodiment, the physiological signal monitor 100 may employ its means of communication to advantageously display acquired information to a user with a recreational purpose. For example, and without limitation, an interface may be provided by a computer program or mobile device application, for which the physiological signal monitoring system may be configured to recognize a user's selected interfacing means and may transmit the acquired physiological data according to the interface detected. The software program/application may be configured to read data sent to it by the physiological signal monitoring system and display the data to the user in such a way that it is meaningful and easy to understand. The data or results of analysis may be displayed on a display screen.

The display screen may be carried by the housing, 101, cradle 102, or other, external device, such as, but not limited to, a cellular phone, tablet, computer, other Internet connected device, or the like. This application may generally have advantageous uses in the realm of individual health and fitness. The interfacing program/application may also be configured to advantageously generate warnings and reports to inform the user of any potential health problems detected by the physiological signal monitoring system. All versions of the interface may be capable of providing different customizable reports of both physiological events and trending.

Figure 21:
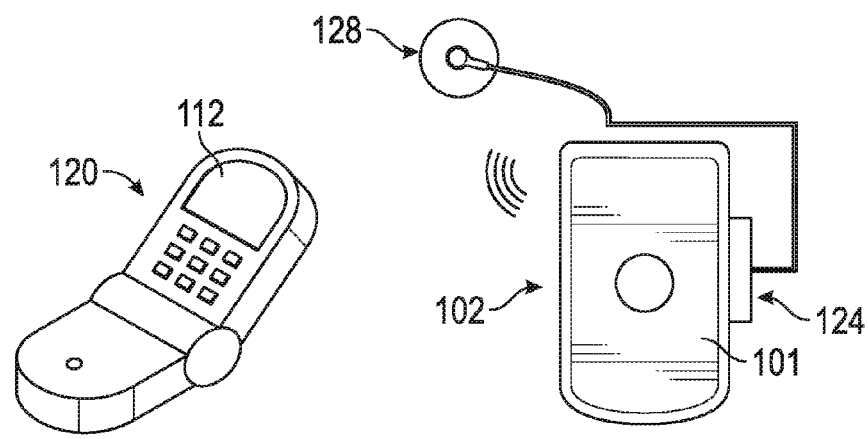
FIG. 21 is an illustration of a physiological signal monitor system, according to one embodiment of the present invention.

FIG. 21 illustrates an embodiment where a housing 101 may communicate with a smart phone 136. The smart phone 136 may include a processor and a memory (not illustrated as they are within the smart phone 136). The smart phone 136 also may include a display screen 112. In the disclosed embodiment, the physiological signal monitor 100 may transmit collected ECG data to the smart phone 136. In some embodiments, the physiological signal monitor 100 may store the collected ECG data in a memory 107 of the housing 101 prior to transmission. The smart phone 136 may operate as a Holter monitor, or may operate as an event monitor. In another embodiment, the smart phone 136 may operate as a mobile cardiac telemetry monitor. In some embodiments, the smart phone 136 may operate as both a Holter monitor and an event monitor. In one embodiment, the housing 101 may wirelessly transmit collected ECG data to the smart phone 136 by a wireless radio 135. The wireless communication between the housing 101 and the smart phone 136 may be accomplished using any one of a variety of different wireless technologies including, for example, and without limitation, 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee.

Figure 22:
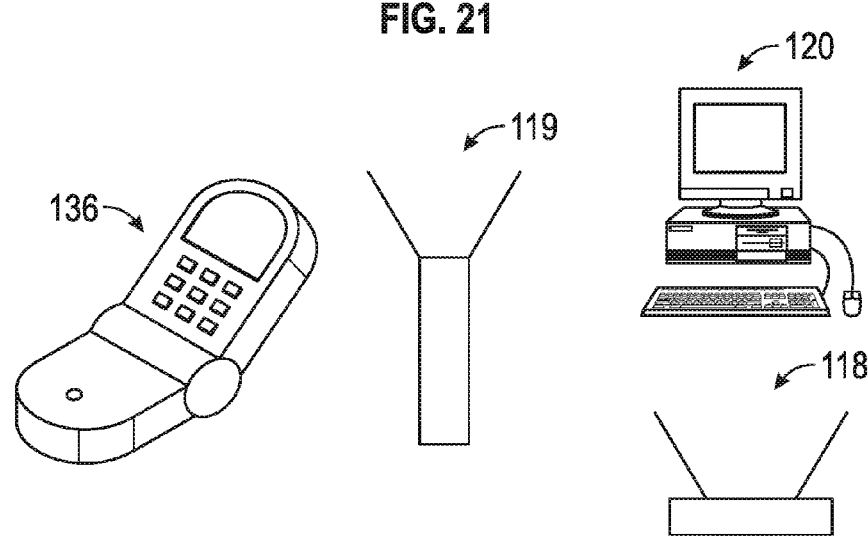
FIG. 22 is an illustration of a physiological signal monitor system, according to one embodiment of the present invention.

FIG. 22 illustrates various communication schemes for the smart phone 136. In some embodiments, the smart phone 136 may transmit data collected from the retractable multi-use cardiac monitor to a monitoring center, as provided by a health professional, a clinic, or a hospital by communicating with a cellular tower 119 of a cellular network. In another embodiment, the smart phone 136 may transmit data to a monitoring center by communicating with a base station 120, which may be a computer, that may include an application which stores and forwards the data to the monitoring center through the Internet (e.g. by email). The application on computer 120 may also be configured to allow a user of the smart phone 136 to print reports of the ECG data collected by the smart phone 136. Communication with the computer 120 may be wired or wireless. For example, and without limitation, the smart phone 136 may plug into the computer 120 using a USB or firewire cable.

In another embodiment, the smart phone 136 may communicate with the computer 120 through a variety of different wireless technologies including, for example, and without limitation, 900 Mhz radio, Bluetooth, IEEE 802.11 (Wi-Fi), WLAN, Personal Area Network, TransferJet, Ultra-wideband (UWB), IrDA, RFID, Wireless USB, Near Field Communication, or ZigBee. In another embodiment, the smart phone 136 simply may transmit collected data to a wireless router 118 which then may transmit the data to the monitoring center through the Internet. The wireless router 118 may support any number of wireless technologies including, for example, and without limitation, IEEE 802.11 (Wi-Fi). In a related embodiment, the smart phone 136 may be configured to detect the presence of the wireless router 118, and when the presence of the wireless router 118 is detected, the smart phone 136 opportunistically may transmit collected data to the wireless router 118 which then may transmit the data to the monitoring center. In yet another embodiment, the smart phone 136 may be configured to transmit data to a monitoring center over a telephone connection by audio modulation. In yet further embodiments, the smart phone 136 may transmit collected data to the monitoring center through any number of intermediaries and through any number of communication technologies.

Figure 23:
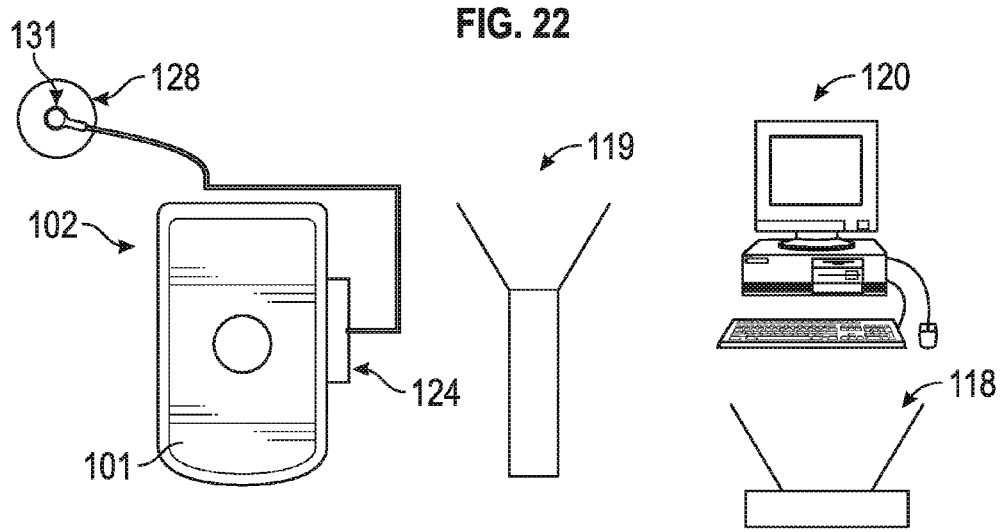
FIG. 23 is an illustration of a physiological signal monitor system, according to one embodiment of the present invention.
Figure 24:
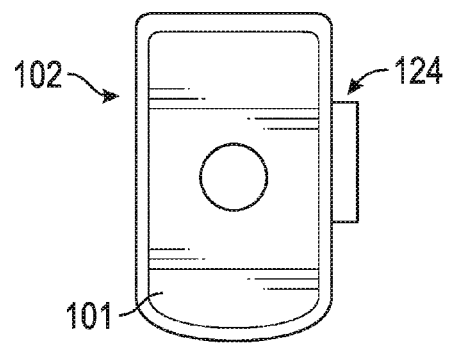
FIG. 24 is a front perspective view of a housing of the physiological signal monitor in combination with the cradle according to an embodiment of the present invention.

FIG. 23 illustrates an embodiment where the physiological signal monitor 100 itself may communicate with a cellular network 119, wireless router 118, or base station 120. The physiological signal monitor 100 may operate as a Holter monitor, or may operate as an event monitor. In another embodiment, the physiological signal monitor 100 may operate as a mobile cardiac telemetry monitor. In some embodiments, the physiological signal monitor 100 may operate as both a Holter monitor and an event monitor. In some embodiments, the physiological signal monitor 100 may be configured to transmit collected ECG data to a monitoring center, as provided by a health professional, a clinic, or a hospital. In some embodiments, the physiological signal monitor 100 may store the collected ECG data in a memory 107 of the housing 101 prior to transmission. In another embodiment, the physiological sensor monitor 100 may include a display screen and the physiological signal monitor 100 may retain any collected ECG data and may display the collected ECG data at a later time. For example, and without limitation, the collected ECG data may later be shown to a doctor or other health professional during a patient visit on a display screen.

Figure 25:
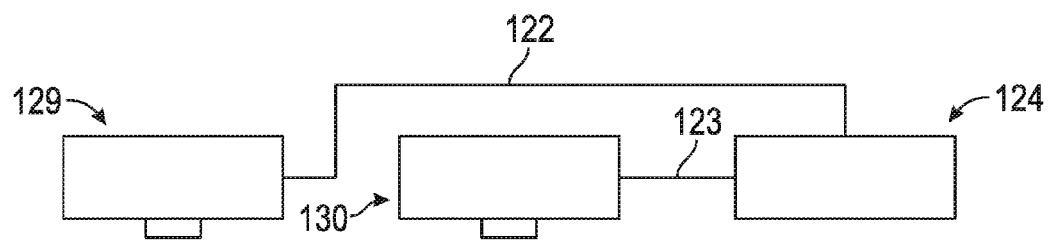
FIG. 25 is a side-view of a wire retractor with electrical contacts extended, according to one embodiment of the present invention.

FIG. 25 is an illustration of an embodiment of a wire retractor 124. The illustrated embodiment includes a first sensing connector 129 and a second sensing connector 130, as well as respective wires 122, 123 interfacing with wire retractors 124.

Figure 26:
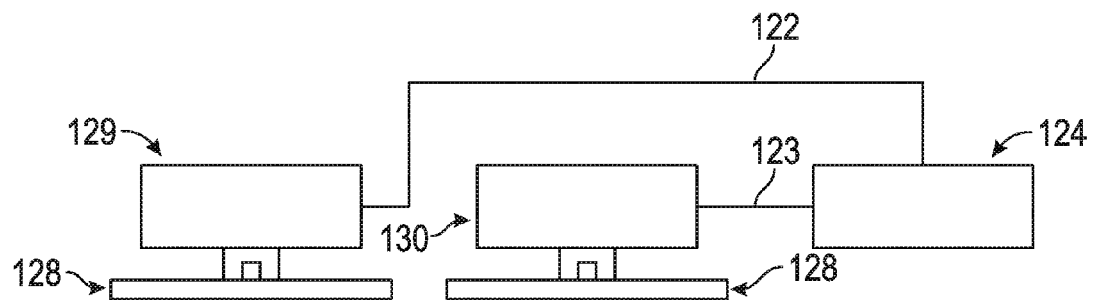
FIG. 26 is a side-view of a wire retractor with electrical contacts extended and electrodes attached, according to one embodiment of the present invention.

FIG. 26 is a side-view of a wire retractor 124, according to one embodiment of the present invention. FIG. 26 illustrates the extractable wires 122, 123 that connect the first sensing connector 129 to the first electrical pad 132 and the second sensing connector 130 to the second electrical pad 133, respectively. FIG. 26 is similar to FIG. 25 with the addition of electrodes 128 connected to the first sensing connector 129 and the second sensing connector 130.

Figure 27:
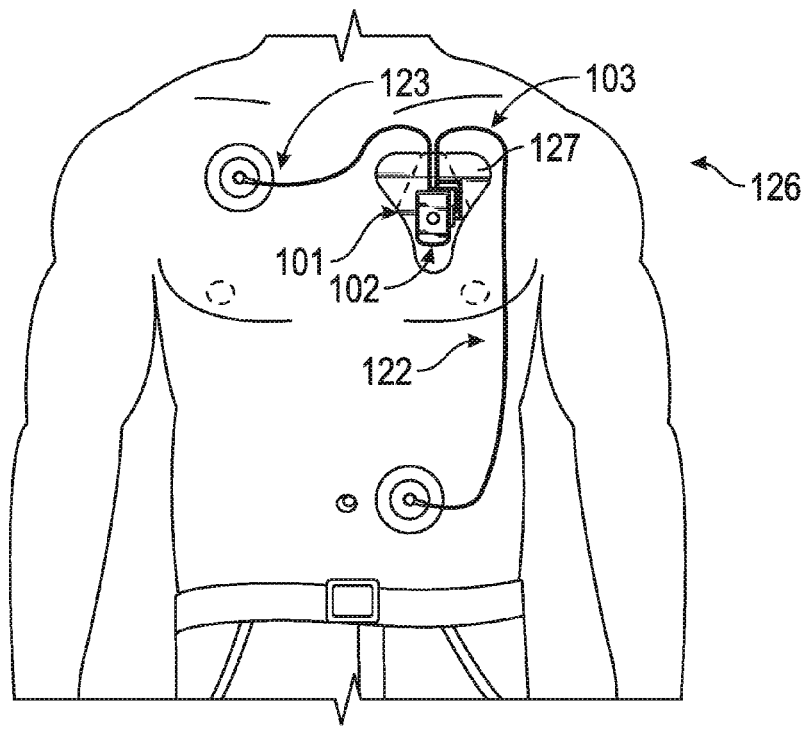
FIG. 27 is an environmental view of the patch as depicted in FIG. 11 secured to a patient, with electrical contacts extended and secured to the patient, in combination with the housing as depicted in FIG. 2 and the cradle depicted in FIG. 17.
Figure 28:
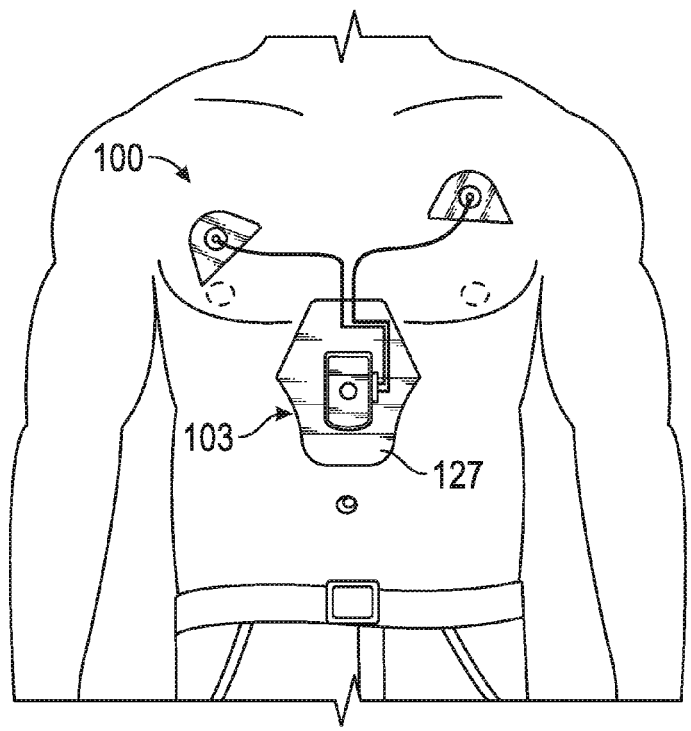
FIG. 28 is an environmental view of the patch as depicted in FIG. 13 secured to a patient, with detachable electrical contacts detached and secured to the patient, in combination with the housing as depicted in FIG. 2 and the cradle as depicted in FIG. 17.

FIGS. 27 and 28 are illustrations of a physiological signal monitor 100 attached to a cardiac monitoring patient 126, according to respective embodiments of the present invention. The physiological signal monitor 100 may be configured to collect ECG signals through the multiple wearable electrodes 128 connected to the patient's 126 skin. Electrodes 128 may be extended away from and retracted toward one another and away from and toward the cradle 102. The retractable nature of the wires 122, 123 also may advantageously allow for easy storage.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated. Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Thus the scope of the invention should be determined by the appended claims and their legal equivalents, and not by the examples given.

That which is claimed is:

1. A physiological signal monitor having retractable wires, the physiological signal monitor comprising:
   a housing comprising:
      a memory,
      a first electrical contact in data communication with the memory,
      a second electrical contact in data communication with the memory, and
      a processor in data communication with the memory;
   a patch comprising an adhesive first side adapted to be secured to a patient and an opposing second side; and
   a cradle, fixedly connected to the second side of the patch, the cradle being adapted to removably carry the housing and further comprising:
      a wire retractor,
      a first electrical pad adapted to contact the first electrical contact,
      a second electrical pad adapted to contact the second electrical contact,
      a first sensing connector,
      a second sensing connector,
      a first wire connecting the first electrical pad to the first sensing connector, wherein the wire retractor is configured to extend and retract the first wire to vary a linear distance between the first electrical pad and the first sensing connector, and
      a second wire connecting the second electrical pad to the second sensing connector, wherein the wire retractor is configured to extend and retract the second wire to vary a linear distance between the second electrical pad and the second sensing connector,
      wherein the first sensing connector and the second sensing connector are configured to collect ECG data and store ECG data onto the memory.

2. The physiological signal monitor according to claim 1 wherein the housing further comprises a symptom button.

3. The physiological signal monitor according to claim 1 wherein the first and second sensing connectors are configured to connect to wearable electrodes.

4. The physiological signal monitor according to claim 1 wherein the first and second sensing connectors are shaped to receive a finger.

5. The physiological signal monitor according to claim 1 further comprising:
   a third sensing connector located on the first side of the patch and configured to collect ECG data and store ECG data onto the memory;
   wherein the housing further comprises a third electrical contact; and
   wherein the cradle further comprises a third electrical pad adapted to contact the third electrical contact and in electrical communication with the third sensing connector.

6. The physiological signal monitor according to claim 1 further comprising a wireless radio configured to transmit a portion of collected ECG data from the memory to a destination.

7. The physiological signal monitor according to claim 6 wherein the destination is a smart phone.

8. The physiological signal monitor according to claim 6 wherein the destination is a monitoring center.

9. The physiological signal monitor according to claim 1 further comprising a display screen that is configured to display collected ECG data.

10. The physiological signal monitor according to claim 1 wherein the housing is detachably connected to the cradle.

11. The physiological signal monitor according to claim 1 wherein housing is adapted to accommodate ten channels of ECG data.

12. The physiological signal monitor according to claim 1 wherein the wire retractor is flexibly connected to the cradle.

13. A physiological signal monitor comprising:
   a housing comprising:
      a memory,
      a first electrical contact in data communication with the memory,
      a second electrical contact in data communication with the memory,
      a third electrical contact, and
      a processor in data communication with the memory,
   a patch comprising an adhesive first side adapted to be secured to a patient and an opposing second side;
   a cradle, fixedly connected to the second side of the patch, the cradle being adapted to removably carry the housing and further comprising:
      a wire retractor,
      a first electrical pad adapted to contact the first electrical contact,
      a second electrical pad adapted to contact the second electrical contact,
      a third electrical pad adapted to contact the third electrical contact,
      a first sensing connector,
      a second sensing connector,
      a first wire connecting the first electrical pad to the first sensing connector, wherein the wire retractor is configured to extend and retract the first wire to vary a linear distance between the first electrical pad and the first sensing connector, and
      a second wire connecting the second electrical pad to the second sensing connector, wherein the wire retractor is configured to extend and retract the second wire to vary a linear distance between the second electrical pad and the second sensing connector, and a third sensing connector located on the first side of the patch and in electrical communication with the third electrical pad;

wherein the first sensing connector, the second sensing connector, and the third sensing connector are configured to collect ECG data and store ECG data onto the memory.

14. The physiological signal monitor according to claim 13 wherein a portion of collected ECG data is transmittable from the memory to a smart phone.

15. The physiological signal monitor according to claim 13 wherein a portion of collected ECG data is transmittable from the memory to a monitoring center.

16. The physiological signal monitor according to claim 13 further comprising a display screen that is configured to display collected ECG data.

17. The physiological signal monitor according to claim 13 wherein the housing is detachably connected to the cradle.

18. The physiological signal monitor according to claim 13 wherein housing is adapted to accommodate ten channels of ECG data.

19. The physiological signal monitor according to claim 13 wherein the wire retractor is flexibly connected to the cradle.

20. A physiological signal monitor, comprising:
a housing comprising:
  a memory,
  a first electrical contact in data communication with the memory, and
  a second electrical contact in data communication with the memory,
  a third electrical contact, and
  a processor in data communication with the memory,
a patch comprising an adhesive first side adapted to be secured to a patient and an opposing second side;
a cradle, fixedly connected to the second side of the patch, the cradle being adapted to removably carry the housing and further comprising:
  a wire retractor,
  a first electrical pad adapted to contact the first electrical contact,
  a second electrical pad adapted to contact the second electrical contact,
  a third electrical pad adapted to contact the third electrical contact,
  a first sensing connector,
  a second sensing connector,
  a first wire connecting the first electrical pad to the first sensing connector, wherein the wire retractor is configured to extend and retract the first wire to vary a linear distance between the first electrical pad and the first sensing connector, and
  a second wire connecting the second electrical pad to the second sensing connector, wherein the wire retractor is configured to extend and retract the second wire to vary a linear distance between the second electrical pad and the second sensing connector,
a third sensing connector located on the first side of the patch and in electrical communication with the third electrical pad; and
a wireless radio configured to transmit a portion of collected ECG data from the memory to a destination;
wherein the first sensing connector, the second sensing connector, and the third sensing connector are configured to collect ECG data and store ECG data onto the memory.

* * * * *